(12) United States Patent
Reddy

(10) Patent No.: US 12,150,667 B1
(45) Date of Patent: Nov. 26, 2024

(54) TISSUE SAMPLE AND SNARE DEVICE

(71) Applicant: Adisesha B. Reddy, Tuscaloosa, AL (US)

(72) Inventor: Adisesha B. Reddy, Tuscaloosa, AL (US)

( * ) Notice: Subject to any disclaimer, the term of this patent is extended or adjusted under 35 U.S.C. 154(b) by 336 days.

(21) Appl. No.: 17/887,440

(22) Filed: Aug. 13, 2022

(51) Int. Cl.
| | |
|---|---|
| *A61B 17/3205* | (2006.01) |
| *A61B 10/02* | (2006.01) |
| *A61B 17/32* | (2006.01) |
| *A61B 17/00* | (2006.01) |

(52) U.S. Cl.
CPC ........ *A61B 17/32056* (2013.01); *A61B 10/02* (2013.01); *A61B 17/320016* (2013.01); *A61B 2010/0208* (2013.01); *A61B 2017/00287* (2013.01); *A61B 2017/00358* (2013.01); *A61B 2017/00367* (2013.01)

(58) Field of Classification Search
CPC .......... A61B 17/221; A61B 2017/2212; A61B 17/32056; A61B 2017/00287; A61B 2017/2215; A61B 17/00234; A61B 17/320016
See application file for complete search history.

(56) References Cited

U.S. PATENT DOCUMENTS

| | | | | |
|---|---|---|---|---|
| 5,759,187 | A * | 6/1998 | Nakao ..................... | A61B 1/018 606/113 |
| 6,007,546 | A * | 12/1999 | Snow ..................... | A61B 18/10 606/113 |
| 7,115,125 | B2 * | 10/2006 | Nakao ..................... | A61B 18/14 606/113 |
| 8,282,572 | B2 * | 10/2012 | Bilsbury .............. | A61B 17/221 600/562 |
| 2007/0016225 | A1 * | 1/2007 | Nakao .................. | A61B 17/221 606/114 |
| 2013/0023895 | A1 * | 1/2013 | Saleh ..................... | A61B 10/04 606/113 |

* cited by examiner

*Primary Examiner* — Katherine M Shi

(74) *Attorney, Agent, or Firm* — Edward P Dutkiewicz

(57) ABSTRACT

There is a main tube with a flexible pull wire guide with a pull wire slidably housed within. A plunger is slidably housed within the main tube, and moves from an open orientation to a close orientation. A specimen snare wire loop is fixedly attached to the end of the pull wire. A basket wire has a loop with an attached specimen basket. The specimen snare loop and the basket wire loop are aligned. The snare wire cuts the specimen, and the basket wire loop and net captures the specimen.

10 Claims, 5 Drawing Sheets

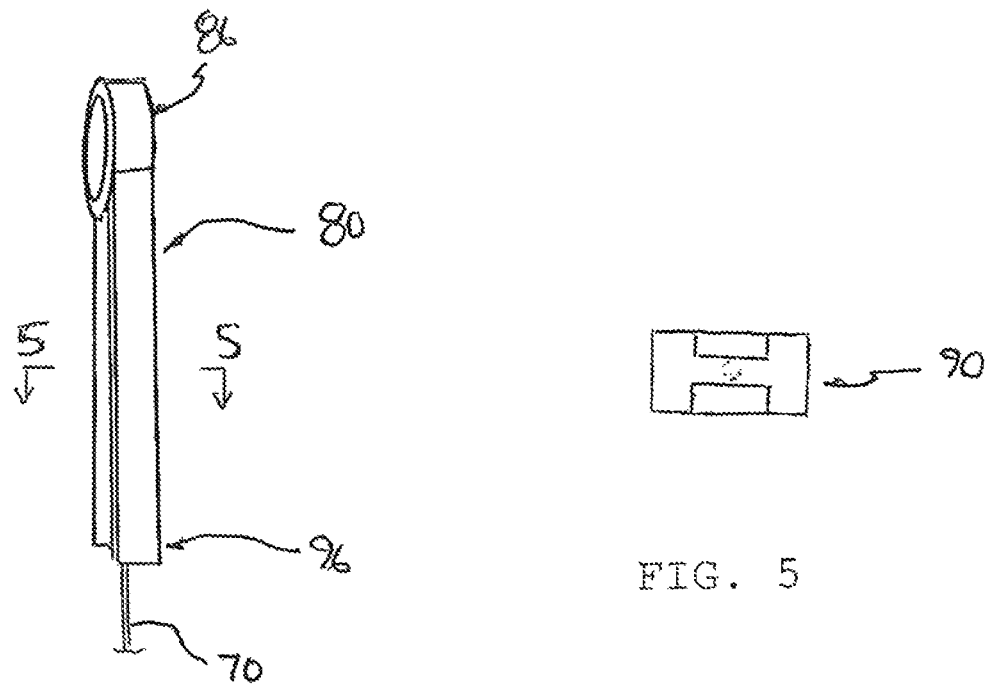
FIG. 4
FIG. 5
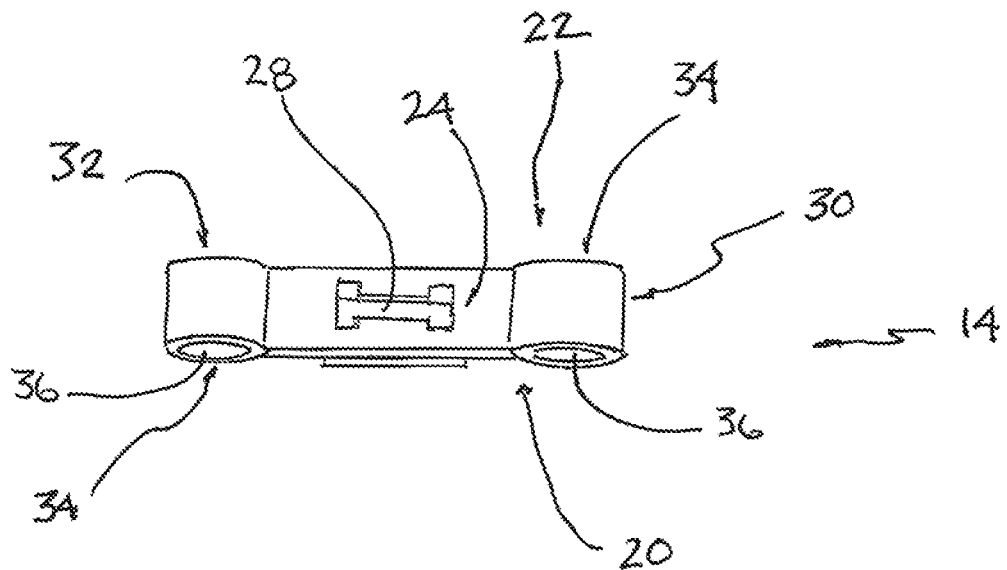
FIG. 6

TISSUE SAMPLE AND SNARE DEVICE

BACKGROUND OF THE INVENTION

Rule 1.78 (F) (1) Disclosure

The Applicant has not submitted a related pending or patented non-provisional application within two months of the filing date of this present application. The invention is made by a single inventor, so there are no other inventors to be disclosed. This application is not under assignment to any other person or entity at this time.

There are no cross referenced or related applications which are direct to, or related to, the present application.

There is no research of development of this application which is federally sponsored.

FIELD OF THE INVENTION

The present invention relates to a tissue sample and snare device and more particularly pertains to collecting tissue samples.

DESCRIPTION OF THE PRIOR ART

The use of tissue collecting devices is known in the prior art. More specifically, tissue collecting devices previously devised and utilized for the purpose of collecting tissue samples are known to consist basically of familiar, expected, and obvious structural configurations, notwithstanding the number of designs encompassed by the prior art which has been developed for the fulfillment of countless objectives and requirements.

While the prior art devices fulfill their respective, particular objectives and requirements, the prior art does not describe tissue sample and snare device that allows collecting tissue samples.

In this respect, the tissue sample and snare device, according to the present invention, substantially departs from the conventional concepts and designs of the prior art, and in doing so provides an apparatus primarily developed for the purpose of conveniently collecting tissue samples.

Therefore, it can be appreciated that there exists a continuing need for a new and improved tissue sample and snare device which can be used for collecting tissue samples. In this regard, the present invention substantially fulfills this need.

SUMMARY OF THE INVENTION

In view of the foregoing disadvantages inherent in the known types of tissue collecting devices now present in the prior art, the present invention provides an improved tissue sample and snare device. As such, the general purpose of the present invention, which will be described subsequently in greater detail, is to provide a new and improved tissue sample and snare device which has all the advantages of the prior art and none of the disadvantages.

In describing this invention, the word "coupled" is used. By "coupled" is meant that the article or structure referred to is joined, either directly, or indirectly, to another article or structure. By "indirectly joined" is meant that there may be an intervening article or structure imposed between the two articles which are "coupled". "Directly joined" means that the two articles or structures are in contact with one another or are essentially continuous with one another.

In describing aspects of the invention, the word "generally" may be used. The term, "generally" when used to describe a configuration means that the configuration includes those aspects which are within normal manufacturing parameters of acceptance. By way of example, the term "generally round" may be used. This should be interpreted to mean that the configuration may be perfectly round, but may also have a radius which is not exact, but is within the manufacturing parameters. For example, a basketball may be generally round, but not be perfectly round.

By adjacent to a structure is meant that the location is near the identified structure.

To attain the objectives of the invention, the present invention essentially comprises a tissue sample and snare device, which comprises several components, in combination, First there is a main tube. The main tube is fabricated of a rigid material such as metal or plastic. The main tube has a proximal upper finger engagement portion, a mid tube portion, and a distal end portion.

The proximal upper finger engagement portion of the main tube comprises a cross bar having a rectilinear configuration. The upper finger engagement portion of the main tube has a front surface, a rear surface, a top surface, and a bottom surface. The cross bar has an H-shaped passageway there through running from the cross bar top surface to the cross bar bottom surface. The cross bar has two opposing ends, being a right end and a left end. The opposing ends of the cross bar each comprise a finger engagement loop. Each cross bar finger engagement loop has an aperture there through.

The mid tube portion of the main tube has a hollow tubular configuration, with a proximal end, a distal end, with a length there between. The mid tube portion of the main tube has a continuous wall. The continuous wall of the mid tube portion has an inner surface which defines a passageway through the length of the mid tube portion. The continuous wall of the mid tube portion has an outer surface. The mid tube portion of the main tube is continuous with the bottom surface of the cross bar of the main tube.

The distal end portion of the main tube comprises an end closure, with a pull wire aperture there through. The distal end portion of the main tube is continuous with the distal end of the mid tube portion of the main tube.

A pull wire guide has a flexible hollow tubular configuration. The pull wire guide has a proximal end and a distal end, with a length there between. The pull wire guide has a continuous wall having an inner surface and an outer surface, with a thickness there between. The pull wire guide inner surface forms a passageway through the length of the pull wire guide. The pull wire guide passageway has an internal diameter.

The proximal end of the pull wire guide is fixedly attached to the distal end portion of the main tube. The passageway of the pull wire guide is continuous with the pull wire aperture of the distal end portion of the main tube. The distal end of the pull wire guide has an end band which is fabricated of a rigid material such as plastic or metal. The end band of the distal end of the pull wire guide has an aperture there through.

A pull wire has a proximal end and a distal end, with a length there between. The pull wire has a diameter. The proximal end of the pull wire has a fixing portion. The distal end of the pull wire has an end crimp.

A plunger is fabricated of a rigid material, such as metal or plastic. The plunger has a proximal portion and a distal portion.

The proximal portion of the plunger has a thumb ring, with the thumb ring of the proximal end of the plunger having a thumb aperture there through.

The distal portion of the plunger comprises an H-shaped shaft, with the H-shaped shaft having a proximal end and a distal end, with a length there between. The proximal end of the distal portion of the plunger is continuous with the thumb ring of the proximal end of the plunger. The distal end of the plunger has a rectilinear end cap. The rectilinear end cap of the distal portion of the plunger has the fixing portion proximal end of the pull wire fixedly attached there to. The plunger passes through the H-shaped aperture of the proximal upper finger engagement portion cross bar.

A specimen snare wire has the pull wire diameter. The specimen snare wire comprises a loop which is fixedly attached to end crimp of the distal end of the pull wire. The specimen snare wire loop has a first length. the specimen snare wire is fixedly attached to the end crimp of the distal end of the pull wire.

Lastly, there is a basket wire having the pull wire diameter. The basket wire comprises a loop, with an attached specimen basket. The basket wire specimen basket comprises a net. The basket wire specimen basket net has an opening which is continuous with the basket wire.

The basket wire loop has a second length, with the second length of the basket wire loop being greater than the first length of the specimen wire loop. The basket wire is fixedly attached to the end crimp of the distal end of the pull wire. The specimen snare loop and the basket wire loop are aligned so that as the pull wire is moved from an open orientation into a closed orientation, the basket wire loop and net is aligned with the snare wire, so as to capture a specimen which is cut by the snare wire.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tissue sample and snare device which has all of the advantages of the prior art tissue collecting devices and none of the disadvantages.

It is another object of the present invention to provide a new and improved tissue sample and snare device which may be easily and efficiently manufactured and marketed.

It is further object of the present invention to provide a new and improved tissue sample and snare device which is of durable and reliable constructions.

An even further object of the present invention is to provide a new and improved tissue sample and snare device which is susceptible of a low cost of manufacture with regard to both materials and labor, and which accordingly is then susceptible of low prices of sale to the consuming public, thereby making such tissue sample and snare device economically available to the buying public.

Even still another object of the present invention is to provide a tissue sample and snare device for collecting tissue samples with a single operation of a plunger.

Lastly, it is an object of the present invention to provide a new and improved tissue sample and snare devicing having a main tube with a flexible pull wire guide with a pull wire slidably housed within. A plunger is slidably housed within the main tube, and moves from an open orientation to a close orientation. A specimen snare wire loop is fixedly attached to the end of the pull wire. A basket wire has a loop with an attached specimen basket. The specimen snare loop and the basket wire loop are aligned. The snare wire cuts the specimen, and the basket wire loop and net captures the specimen.

It should be understood that while the above-stated objects are goals which are sought to be achieved, such objects should not be construed as limiting or diminishing the scope of the claims herein made.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a right side perspective of the plunger with the pull wire attached there to.

FIG. 5 is a view along line 5-5 of FIG. 4.

FIG. 6 is a top perspective view of the cross bar of the main tube.

The same reference numerals refer to the same parts throughout the various Figures.

DESCRIPTION OF THE PREFERRED EMBODIMENT

Figure 1:
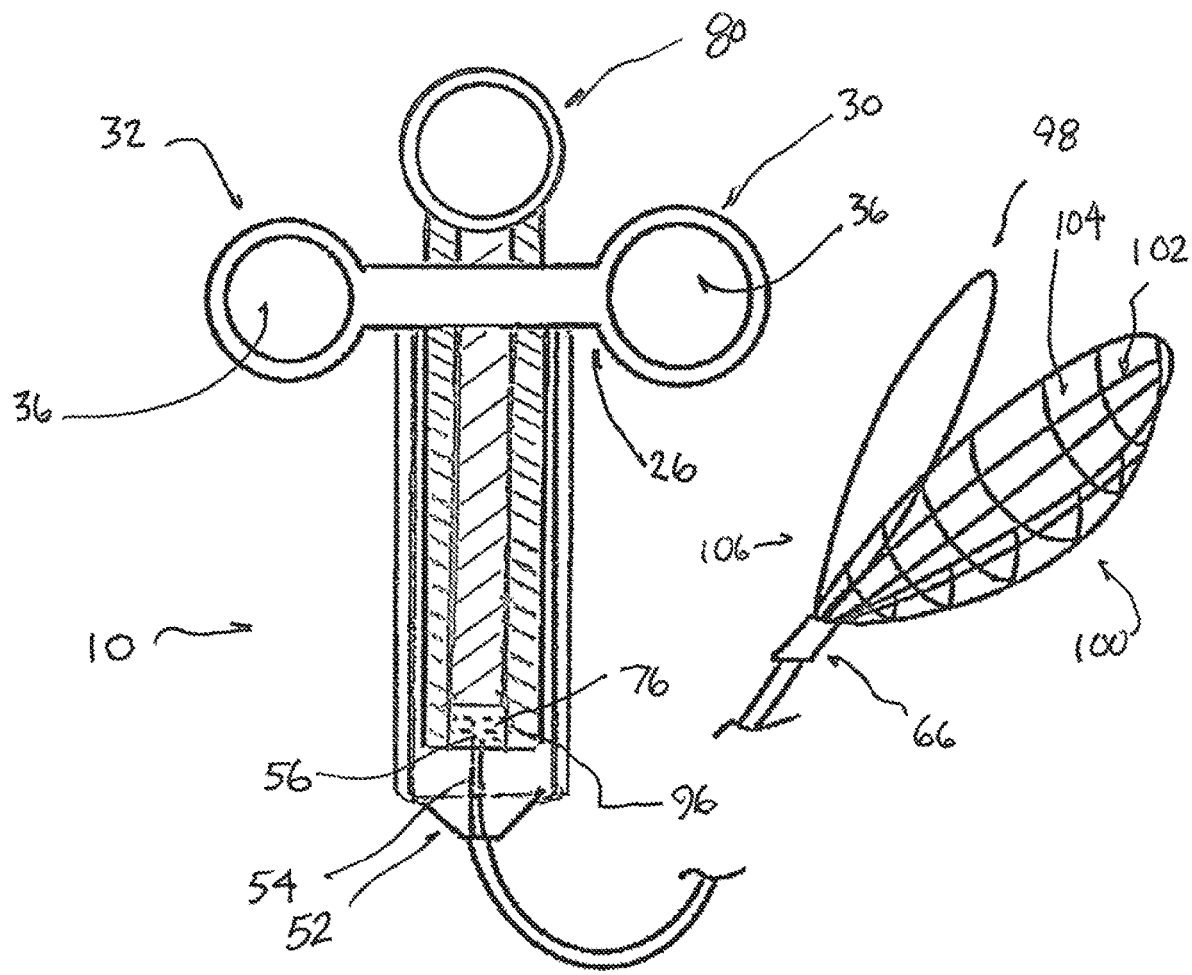
FIG. 1 is cross sectional view of the device, showing the plunger and snare/basket in the open orientation.
Figure 2:
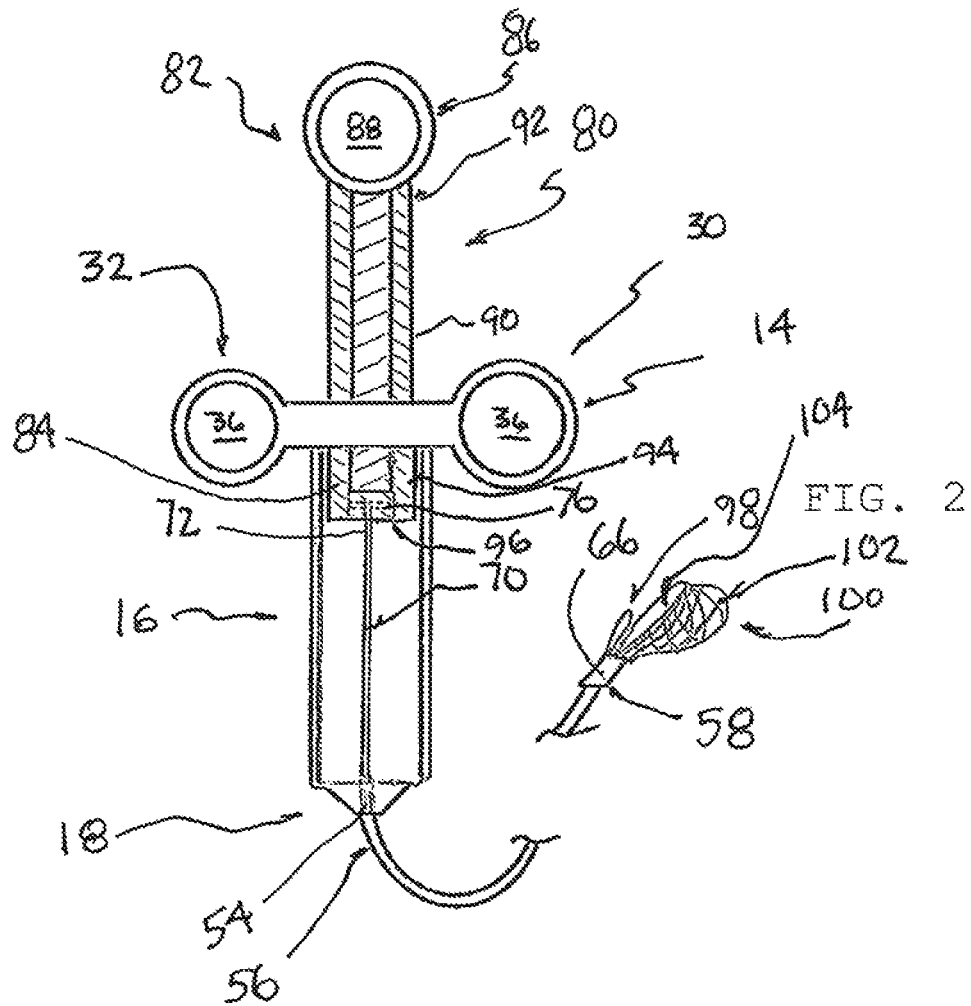
FIG. 2 is cross sectional view of the device, showing the plunger and snare/basket in the closed orientation.
Figure 3:
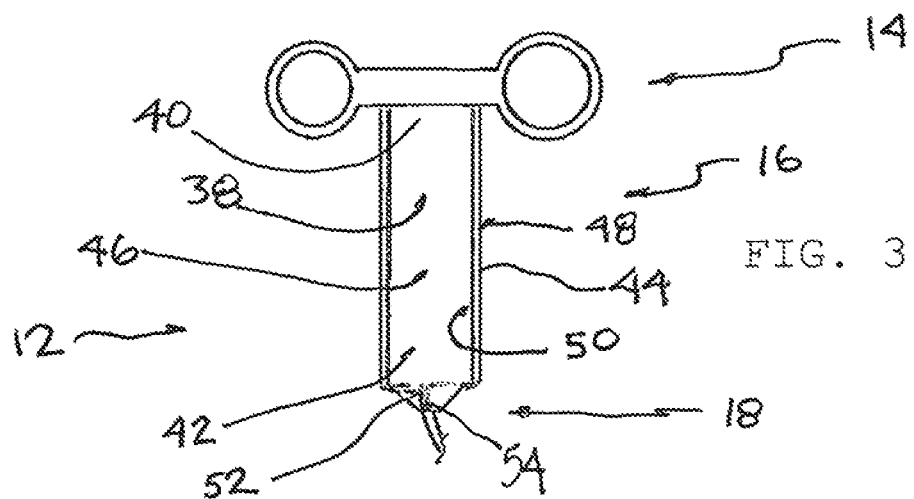
FIG. 3 is a cross sectional view of the device, showing the main tube.
Figure 7:
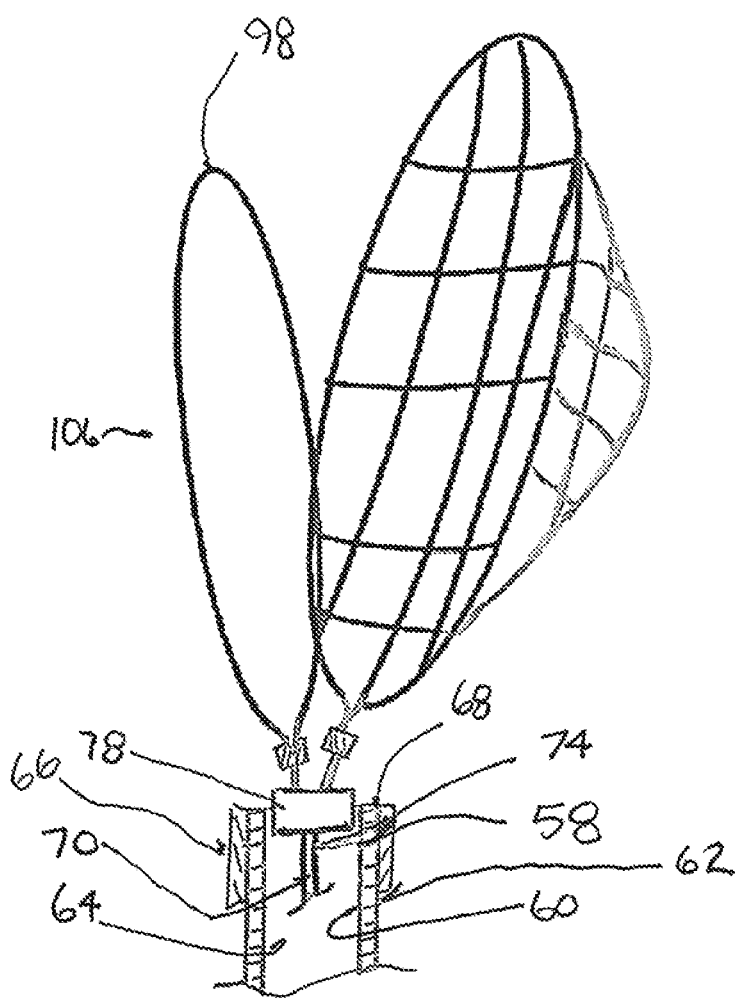
FIG. 7 is a close up view of the snare and basket located at the distal end of the pull wire guide, showing part of the pull wire with the attached snare and basket.
Figure 8:
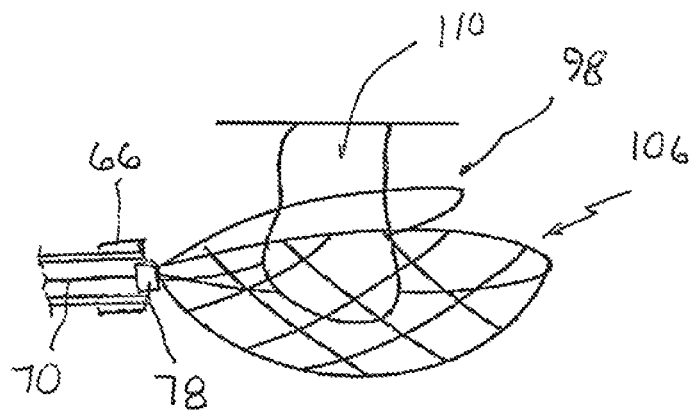
FIG. 8 is cross sectional view of the distal end of the pull wire guide, showing the open orientation of the snare and basket before actuation of the plunger. Note the snare position and the basket position in relation to the tissue.
Figure 9:
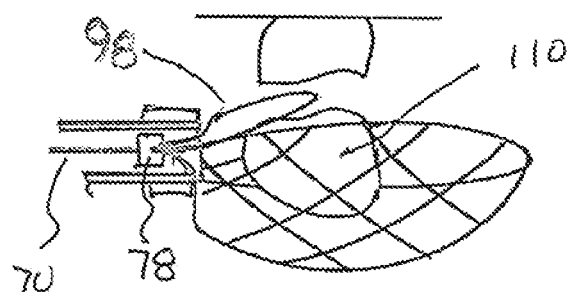
FIG. 9 is a cross sectional view of distal end of the pull wire guide, showing the pulling of the snare and basket as the plunger is actuated, with the snare cutting off a specimen of the tissue. Note the snare position and the basket position in alignment with each other, in relation to the tissue specimen.
Figure 10:
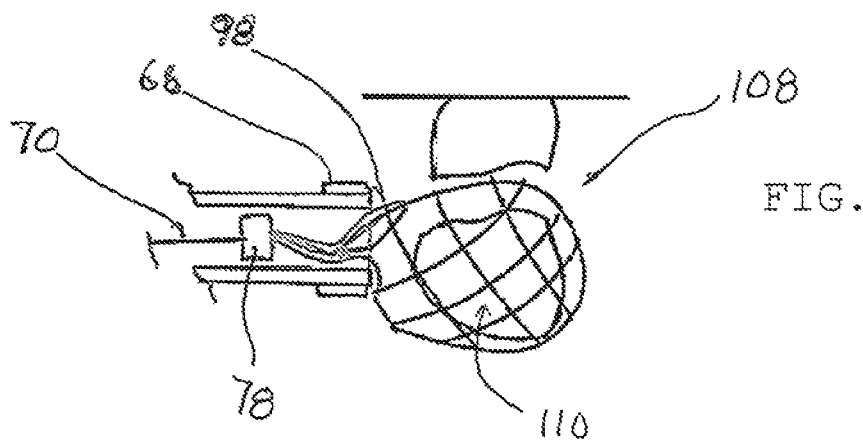
FIG. 10 is a cross sectional view of distal end of the pull wire guide, showing the pulling of the snare and basket as the plunger is pulled into a closed orientation, with the snare cutting off a specimen of the tissue and being pulled into the pull wire guide. Note basket position is pulled closed, trapping the tissue specimen in the netting of the basket.

With reference now to the drawings, and in particular to FIG. 1 thereof, the preferred embodiment of the new and improved tissue sample and snare device embodying the principles and concepts of the present invention and generally designated by the reference numeral 10 will be described.

The present invention, the tissue sample and snare device 10 is comprised of a plurality of components. Such components in their broadest context include a main tube, a plunger, a pull wire and a snare and basket combination. Such components are individually configured and correlated with respect to each other so as to attain the desired objective.

Herein described is a tissue sample and snare device, which comprises several components, in combination, First there is a main tube 12. The main tube is fabricated of a rigid material such as metal or plastic. The main tube has a proximal upper finger engagement portion 14, a mid tube portion 16, and a distal end portion 18.

The proximal upper finger engagement portion of the main tube comprises a cross bar having a rectilinear configuration. The upper finger engagement portion of the main tube has a front surface 20, a rear surface 22, a top surface 24, and a bottom surface 26. The cross bar has an H-shaped passageway 28 there through running from the cross bar top surface to the cross bar bottom surface. The cross bar has two opposing ends, being a right end 30 and a left end 32. The opposing ends of the cross bar each comprise a finger engagement loop 34. Each cross bar finger engagement loop has an aperture 36 there through.

The mid tube portion of the main tube has a hollow tubular configuration 38, with a proximal end 40, a distal end 42, with a length there between. The mid tube portion of the main tube has a continuous wall 44. The continuous wall of the mid tube portion has an inner surface which defines a passageway 46 through the length of the mid tube portion. The continuous wall of the mid tube portion has an outer surface 48 and an inner surface 50. The mid tube portion proximal end of the main tube is continuous with the bottom surface of the cross bar of the main tube.

The distal end portion of the main tube comprises an end closure 52, with a pull wire aperture 54 there through. The distal end portion of the main tube is continuous with the distal end of the mid tube portion of the main tube.

A pull wire guide has a flexible hollow tubular configuration. The pull wire guide has a proximal end 56 and a distal end 58, with a length there between. The pull wire guide has a continuous wall having an inner surface 60 and an outer surface 62, with a thickness there between. The pull wire guide inner surface forms a passageway 64 through the length of the pull wire guide. The pull wire guide passageway has an internal diameter.

The proximal end of the pull wire guide is fixedly attached to the distal end portion of the main tube. The passageway of the pull wire guide is continuous with the pull wire aperture of the distal end portion of the main tube. The distal end of the pull wire guide has an end band 66 which is fabricated of a rigid material such as plastic or metal. The end band of the distal end of the pull wire guide has an aperture 68 there through so as to allow the end band to fit fixedly around the distal end of the pull wire guide.

A pull wire 70 has a proximal end 72 and a distal end 74, with a length there between. The pull wire has a diameter. The proximal end of the pull wire has a fixing portion 76. The distal end of the pull wire has an end crimp 78.

A plunger 80 is fabricated of a rigid material, such as metal or plastic. The plunger has a proximal portion 82 and a distal portion 84.

The proximal portion of the plunger has a thumb ring 86, with the thumb ring of the proximal end of the plunger having a thumb aperture 88 there through.

The distal portion of the plunger comprises an H-shaped shaft 90, with the H-shaped shaft having a proximal end 92 and a distal end 94, with a length there between. The proximal end of the distal portion of the plunger is continuous with the thumb ring of the proximal end of the plunger. The distal end of the plunger has a rectilinear end cap 96. The rectilinear end cap of the distal portion of the plunger has the fixing portion proximal end of the pull wire fixedly attached there to.

A specimen snare wire 98 has the pull wire diameter. The specimen snare wire comprises a loop which is fixedly attached to end crimp of the distal end of the pull wire. The specimen snare wire loop has a first length. the specimen snare wire is fixedly attached to the end crimp of the distal end of the pull wire.

Lastly, there is a basket wire 100 having the pull wire diameter. The basket wire comprises a loop, with an attached specimen basket 102. The basket wire specimen basket comprises a net. The basket wire specimen basket net has an opening 104 which is continuous with the basket wire.

The basket wire loop has a second length, with the second length of the basket wire loop being greater than the first length of the specimen wire loop. The basket wire is fixedly attached to the end crimp of the distal end of the pull wire. The specimen snare loop and the basket wire loop are aligned so that as the pull wire is moved from an open orientation 106 into a closed orientation 108, the basket wire loop and net is aligned with the snare wire, so as to capture a specimen 110 which is cut by the snare wire.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A tissue sample and snare device, comprising, in combination:

a main tube having a proximal upper finger engagement portion and a mid tube portion and a distal end portion, the proximal upper finger engagement portion of the main tube comprising a cross bar with a front surface and a rear surface and a top surface and a bottom surface, the cross bar having a passageway there through, the mid tube portion of the main tube having a hollow tubular configuration with a proximal end and a distal end with a length there between, the distal end portion of the main tube comprising an end closure with a pull wire aperture there through;

a pull wire guide having a flexible hollow tubular configuration, the pull wire guide having a proximal end and a distal end with a length there between, the pull wire guide having a continuous wall having an inner surface and an outer surface with a thickness there between, the pull wire guide inner surface forming a passageway through the length of the pull wire guide;

a pull wire having a proximal end and a distal end with a length there between, the pull wire having a diameter, the proximal end of the pull wire having a fixing portion and the distal end of the pull wire having an end crimp;

a plunger having a proximal portion and a distal portion, with the distal portion of the plunger comprising a proximal end and a distal end with a length there between, the distal end of the distal portion of the plunger having an end cap, with the end cap of the distal portion of the plunger having the fixing portion of the proximal end of the pull wire fixedly attached there to, the plunger passing through the proximal upper finger engagement portion cross bar;

a specimen snare wire comprising a loop which is fixedly attached to the end crimp of the distal end of the pull wire; and a basket wire comprising a loop with an attached specimen basket, the basket wire specimen basket comprising a net with an opening which is continuous with the loop, the specimen snare wire loop and the basket wire loop being aligned so that as the pull wire is moved from an open orientation into a closed orientation, the basket wire loop and net is aligned with the snare wire so as to capture a specimen which is cut by the snare wire, and the basket wire being fixedly attached to the end crimp of the distal end of the pull wire.

2. The tissue sample and snare device, as described in claim 1, the device further comprising:

the basket wire loop having a second length, with the second length of the basket wire loop being greater than a first length of the specimen snare wire loop.

3. The tissue sample and snare device, as described in claim 2, the device further comprising:

the cross bar having two opposing ends, being a right end and a left end;

the mid tube portion of the main tube having a continuous wall, the distal portion of the plunger comprising an H-shaped shaft; and the end cap of the distal end of the distal portion of the plunger having a rectilinear configuration.

4. The tissue sample and snare device, as described in claim 3, the device further comprising:

the opposing ends of the cross bar each comprising a finger engagement loop, with each cross bar finger engagement loop having an aperture there through;

the continuous wall of the mid tube portion having an inner surface which defines a passageway through the mid tube portion, the continuous wall of the mid tube portion having an outer surface; and the distal end portion of the main tube being continuous with the distal end of the mid tube portion of the main tube.

5. The tissue sample and snare device, as described in claim 4, the device further comprising:

the mid tube portion of the main tube being continuous with the bottom surface of the cross bar of the main tube;

the pull wire guide passageway having an internal diameter, the passageway of the pull wire guide being continuous with the pull wire aperture of the distal end portion of the main tube; and the proximal portion of the plunger having a thumb ring with the thumb ring of the proximal end of the plunger having a thumb aperture there through.

6. The tissue sample and snare device, as described in claim 5, the device further comprising:

the cross bar having a rectilinear configuration; the distal end of the pull wire guide having an end band, the end band of the distal end of the pull wire guide having an aperture there through; and the proximal end of the distal portion of the plunger being continuous with the thumb ring of the proximal end of the plunger.

7. The tissue sample and snare device, as described in claim 6, the device further comprising the cross bar passageway being an H-shaped passageway, the H-shaped passageway running from the cross bar top surface to the cross bar bottom surface.

8. The tissue sample and snare device, as described in claim 7, the device further comprising:

the main tube fabricated of a rigid material;

the proximal end of the pull wire guide being fixedly attached to the distal end portion of the main tube;

the end band of the distal end of the pull wire guide being fabricated of a rigid material;

the plunger being fabricated of a rigid material;

the specimen snare wire having the pull wire diameter; and the basket wire having the pull wire diameter.

9. A tissue sample and snare device, comprising, in combination:

a main tube having a proximal upper finger engagement portion comprising a cross bar with an aperture there through, and a mid tube portion having a length and a distal end portion comprising an end closure with a pull wire aperture there through;

a flexible pull wire guide having a passageway there through;

a pull wire having a proximal end and a distal end with a length there between, the proximal end of the pull wire having a fixing portion and the distal end of the pull wire having an end crimp;

a plunger having a proximal portion and a distal portion, with the distal portion of the plunger comprising a proximal end and a distal end with a length there between, the distal end of the distal portion of the plunger having an end cap, with the end cap of the distal portion of the plunger having the fixing portion of the proximal end of the pull wire fixedly attached thereto;

a specimen snare wire comprising a loop which is fixedly attached to the end crimp of the distal end of the pull wire; and a basket wire comprising a loop with an attached specimen basket, the basket wire specimen basket comprising a net with an opening which is continuous with the loop, the specimen snare wire loop and the basket wire loop being aligned so that as the pull wire is moved from an open orientation into a closed orientation, the basket wire loop and net is aligned with the snare wire so as to capture a specimen which is cut by the snare wire, and the basket wire being fixedly attached to the end crimp of the distal end of the pull wire.

10. The tissue sample and snare device, as described in claim 9, the device further comprising the plunger being sized to be slidably received within the mid tube portion of the main tube, the plunger passing through an H-shaped aperture of the proximal upper finger engagement portion cross bar.

\* \* \* \* \*